United States Patent
Sugiyama (10) Patent No.: US 12,274,573 B2
(45) Date of Patent: Apr. 15, 2025

(54) WALL THICKNESS ESTIMATION METHOD, RECORDING MEDIUM, WALL THICKNESS ESTIMATION DEVICE, AND WALL THICKNESS ESTIMATION SYSTEM

(71) Applicant: OSAKA UNIVERSITY, Osaka (JP)

(72) Inventor: Yoshie Sugiyama, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 0 days.

(21) Appl. No.: 18/008,334

(22) PCT Filed: Aug. 19, 2021

(86) PCT No.: PCT/JP2021/030465
§ 371 (c)(1),
(2) Date: Dec. 5, 2022

(87) PCT Pub. No.: WO2023/021671
PCT Pub. Date: Feb. 23, 2023

(65) Prior Publication Data
US 2024/0225577 A1    Jul. 11, 2024

(51) Int. Cl.
*A61B 6/50* (2024.01)
*G06T 7/00* (2017.01)
*G06T 7/62* (2017.01)

(52) U.S. Cl.
CPC .............. *A61B 6/504* (2013.01); *A61B 6/501* (2013.01); *G06T 7/0016* (2013.01); *G06T 2207/10016* (2013.01); *G06T 2207/30101* (2013.01)

(58) Field of Classification Search
CPC ........... A61B 6/504; A61B 6/501; A61B 6/00; A61B 6/5217; A61B 6/03; G06T 7/0016;
(Continued)

(56) References Cited

U.S. PATENT DOCUMENTS

2004/0049484 A1   3/2004  Kamba
2014/0316758 A1*  10/2014 Yagi ................. A61B 5/026
                                                                 703/9

FOREIGN PATENT DOCUMENTS

JP   2004-41670     2/2004
JP   2013-118932    6/2013
WO   2021/019809    2/2021

OTHER PUBLICATIONS

Isaksen et al. "Determination of Wall Tension in Cerebral Artery Aneurysms by Numerical Simulation"; 2008, American Heart Association, Inc.; pp. 3172-3178. (Year: 2008).*

(Continued)

*Primary Examiner* — Siamak Harandi
(74) *Attorney, Agent, or Firm* — Wenderoth, Lind & Ponack, L.L.P.

(57) ABSTRACT

A wall thickness estimation method includes: obtaining behavioral information based on a video in which an organ wall or a blood vessel wall is captured using four-dimensional angiography, the behavioral information being numerical information about changes over time in a position of each of a plurality of predetermined points in the organ wall or the blood vessel wall; generating, based on the behavioral information obtained in the obtaining, estimation information that visualizes mass of each of the plurality of predetermined points for estimating a thickness of the organ wall or a thickness of the blood vessel wall; and outputting the estimation information generated in the generating.

11 Claims, 8 Drawing Sheets

(58) Field of Classification Search
CPC . G06T 2207/10016; G06T 2207/30101; G06T 7/62

See application file for complete search history.

(56) References Cited

OTHER PUBLICATIONS

Singh et al. "Mechanical properties of whole-body soft human tissues: a review"; Oct. 19, 2021; Biomedical Materials, 16(2021) pp. 1-21 (Year: 2021).*

Gradus-Pizlo et al. "Left Anterior Descending Coronary Artery Wall Thickness Measured by High-Frequency Transthoracic and Epicardial Echocardiography"; 2003; Excepta Medica, Inc.; pp. 27-32 (Year: 2003).*

International Search Report issued Oct. 26, 2021 in International (PCT) Application No. PCT/JP2021/030465.

* cited by examiner

WALL THICKNESS ESTIMATION METHOD, RECORDING MEDIUM, WALL THICKNESS ESTIMATION DEVICE, AND WALL THICKNESS ESTIMATION SYSTEM

TECHNICAL FIELD

The present invention relates to a wall thickness estimation method and the like. The method is for estimating a thickness of an organ wall or a thickness of a blood vessel wall.

BACKGROUND ART

A cerebral aneurysm, which is one vascular disease, is an extremely high-risk disease with a fatality rate of more than 50% once it ruptures, and the cerebral aneurysm is also a socially significant disease due to its high rate of aftereffect. For this reason, prophylactic treatment (preemptive medicine) to prevent rupture of cerebral aneurysms is very important, and proper therapeutic intervention is essential.

For proper treatment, it is useful to know information about (for example, the thickness of) the wall of the cerebral aneurysm. This is because it is known that a cerebral aneurysm is more likely to rupture in areas with thin walls than in areas with thick walls. However, even within a single aneurysm, the geometry, including the thickness, of the aneurysm wall varies from aneurysm to aneurysm.

It is therefore difficult even for experts to infer information about the geometry, including the thickness, of the aneurysm wall only from the shape of the lumen or the like of the aneurysm wall obtained by computed tomography (CT), magnetic resonance imaging (MRI), and magnetic resonance angiography (MRA).

For example, one known method of measuring the thickness of the wall of a cerebral aneurysm is imaging or visual inspection in craniotomy performed by a doctor. However, this method is highly invasive, places a heavy burden on the patient, and is not a method by which the thickness of the wall of a cerebral aneurysm can be easily measured.

One example of a known minimally invasive method of measuring the thickness of a blood vessel wall, such as the wall of a cerebral aneurysm, is the ultrasonic diagnostic apparatus disclosed in Patent Literature (PTL) 1. PTL 1 discloses an ultrasonic diagnostic apparatus that generates image data using ultrasonic signals and displays information about the thickness of a blood vessel wall of a subject based on the image data.

CITATION LIST

Patent Literature

[PTL 1] Japanese Unexamined Patent Application Publication No. 2013-118932

SUMMARY OF INVENTION

Technical Problem

Unfortunately, the image data obtained using the conventional technique disclosed in PTL 1 is less precise, and therefore, it is difficult to obtain highly accurate information about the blood vessel wall. Furthermore, it is difficult to obtain highly accurate information about not only the blood vessel wall but also an organ wall in a human body and propose information for providing specific treatments for organ diseases or blood vessel diseases according to the conventional technique.

In view of this, the present invention has an object to provide a method and the like that can generate highly accurate information about the organ wall or the blood vessel wall using a minimally invasive method, thereby providing useful information for applying specific treatments for organ diseases or blood vessel diseases.

Solution to Problem

A wall thickness estimation method according to an aspect of the present invention includes obtaining behavioral information based on a video in which an organ wall or a blood vessel wall is captured using four-dimensional angiography, the behavioral information being numerical information about changes over time in a position of each of a plurality of predetermined points in the organ wall or the blood vessel wall; generating, based on the behavioral information obtained in the obtaining, estimation information that visualizes mass of each of the plurality of predetermined points for estimating a thickness of the organ wall or a thickness of the blood vessel wall; and outputting the estimation information generated in the generating.

A non-transitory recording medium having a computer program according to one aspect of the present invention recorded thereon. The computer program is for causing a computer to execute the above-described wall thickness estimation method.

Furthermore, a wall thickness estimation device according to an aspect of the present invention includes an obtainer which obtains behavioral information based on a video in which an organ wall or a blood vessel wall is captured using four-dimensional angiography, the behavioral information being numerical information about changes over time in a position of each of a plurality of predetermined points in the organ wall or the blood vessel wall; a generator which generates, based on the behavioral information obtained by the obtainer, estimation information that visualizes mass of each of the plurality of predetermined points for estimating a thickness of the organ wall or a thickness of the blood vessel wall; and an outputter which outputs the estimation information generated in the generating.

Furthermore, a wall thickness estimation system according to an aspect of the present invention the wall thickness estimation device; a video information processing device which obtains the video, generates the behavioral information, and outputs the behavioral information to the obtainer; and a display which displays the estimation information output by the outputter.

Advantageous Effects of Invention

With the blood vessel wall thickness estimation method and the like according to the present invention, it is possible to generate highly accurate information about the organ wall or the blood vessel wall using a minimally invasive method, thereby providing useful information for applying specific treatments for organ diseases or blood vessel diseases.

DESCRIPTION OF EMBODIMENTS

Hereinafter, embodiments are described with reference to the drawings. Each of the following embodiments describes a general or specific example. The numerical values, shapes, materials, elements, the arrangement and connection of the elements, steps, the order of the steps etc., presented in the following embodiments are mere examples, and do not limit the scope of the present invention. Among the elements in the following embodiments, those not recited in any one of the independent claims are described as optional elements.

It is to be noted that the diagrams are schematic drawings, and are not necessarily exactly illustrated. In the diagrams, substantially the same elements are assigned with the same numerical references. Accordingly, overlapping descriptions thereof are omitted or simplified.

EMBODIMENT

[Configuration of Wall Thickness Estimation System]

Figure 1:
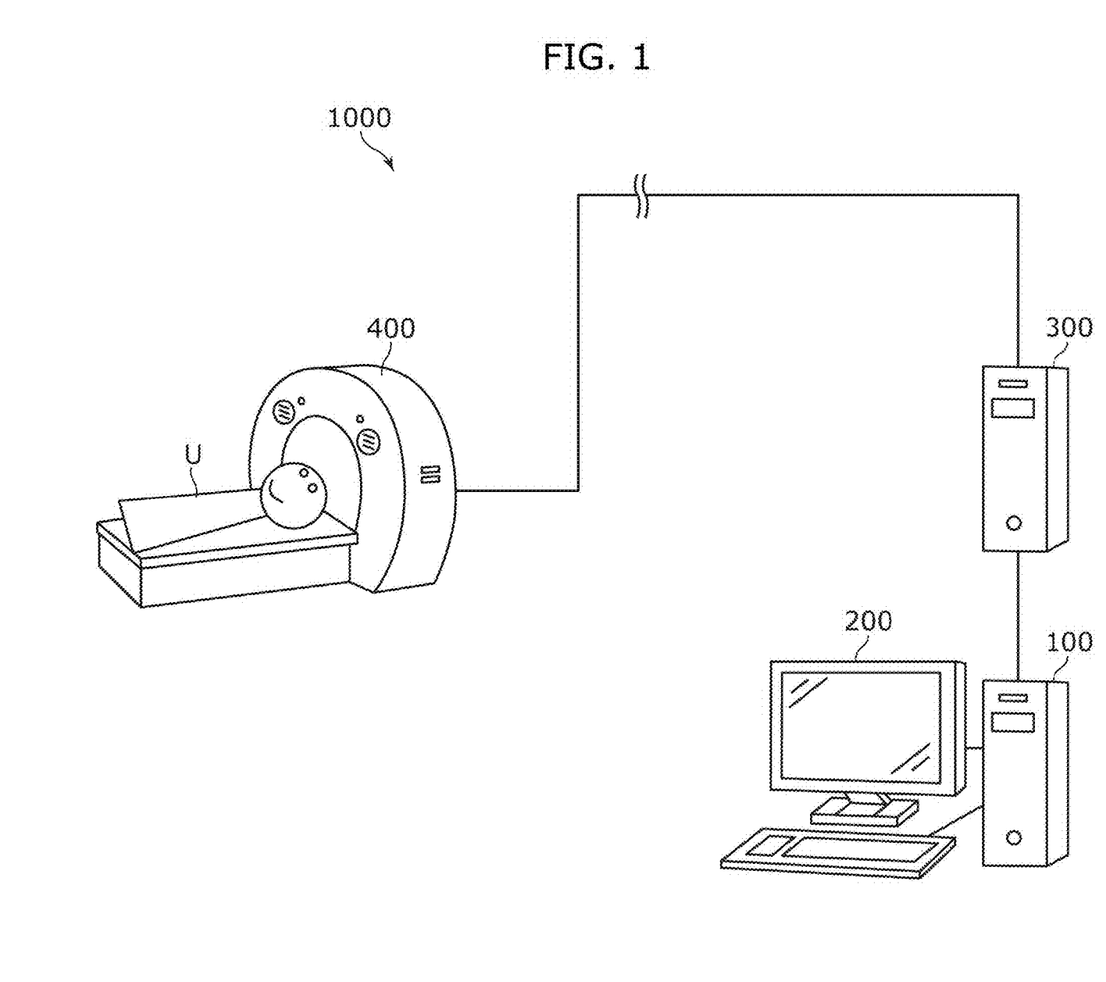
FIG. 1 is a diagram illustrating the configuration of a wall thickness estimation system according to an embodiment.

First, the configuration of wall thickness estimation system 1000 according to an embodiment is described. FIG. 1 is a diagram illustrating the configuration of wall thickness estimation system 1000 according to the embodiment.

Wall thickness estimation system 1000 is a system that uses four-dimensional angiography to obtain behavioral information, which is numerical information about changes over time in the position of each of predetermined points, from a video in which an organ wall or a blood vessel wall of subject U is captured. Wall thickness estimation system 1000 further generates, for each position, estimation information for estimating the thickness of the organ wall or the thickness of the blood vessel wall based on the behavioral information obtained. For example, wall thickness estimation system 1000 estimates a thickness of a cerebral aneurysm which is one example of a blood vessel wall in subject U.

Four-dimensional angiography is a technique that adds a time axis to three-dimensional angiography. Three-dimensional angiography is a technique that collects three-dimensional data on blood vessels using an X-ray CT device or an MRI device, and extracts vascular information. Four-dimensional angiography using an X-ray CT device is also referred to as four-dimensional computed tomography angiography (4DCTA)

A video is obtained through four-dimensional angiography. The video is a time series of three or more still images, and may be, for example, a video obtained over n pulses of the heart (n is a natural number). For example, the video may be a video within a predetermined time period. For example, the predetermined time period may be m seconds (m is a natural number).

Here, an organ wall is a wall of an organ, and organs include chest organs and abdominal organs. For example, chest organs include a heart, lungs, etc., and abdominal organs include a stomach, intestines, a liver, kidneys, a pancreas, etc., but examples of chest organs and abdominal organs are not limited thereto. In addition, organs may include chest organs each having a lumen and abdominal organs each having a lumen.

A wall of an organ may be, for example, a wall that divides the organ and other organs. As one example, when the organ is a heart, an organ wall is a wall defined by muscles (myocardium) that divides the heart and the other organs. The organ wall may be, for example, a wall that divides regions in the organ. As one example, when the organ is a heart, the organ wall is the interventricular septum that divides the left ventricle and the right ventricle which are examples of regions in the heart.

The thickness of the blood vessel wall may be the thickness of a wall of the blood vessel that is an artery or a vein and may be the thickness of the wall of an aneurysm or a wall of a varicose vein. For example, the thickness of the blood vessel wall may be the thickness of the wall of a cerebral aneurysm, an aortic aneurysm, or an organ.

As illustrated in FIG. 1, blood vessel wall thickness estimation system 1000 includes wall thickness estimation device 100, display 200, video information processing device 300, and video capturing device 400.

Video capturing device 400 is a device that generates a video in which an organ wall or a blood vessel wall is captured using four-dimensional angiography. Video capturing device 400 is, for example, an X-ray CT device or an MRI device. In this embodiment, video capturing device 400 is an X-ray CT device, and video capturing device 400 includes an X-ray tube that irradiates X-rays, a detector that receives signals, and a computer.

The detector is located opposite the X-ray tube and detects the X-rays after they have passed through the body of subject U. Using the fact that the absorption of X-rays differs depending on the part of the body of subject U, the computer generates a video including the organ wall or the blood vessel wall in a specific part of the body of subject U. It is to be noted that video capturing device 400 has a function of measuring and obtaining an electrocardiographic complex of subject U.

Unlike techniques such as abdominal operation, open heart surgery, and craniotomy, the technique of using an X-ray CT device or an MRI device and four-dimensional angiography is a minimally invasive technique because it does not require an incision or the like that places a large burden on the body of subject U. Moreover, the technique of using the X-ray CT device or the MRI device and four-dimensional angiography can generate highly precise videos.

Video information processing device 300 obtains a video in which an organ wall or a blood vessel wall is captured using four-dimensional angiography generated by video capturing device 400, and generates behavioral information which is numerical information about changes over time in the position of each of a plurality of predetermined points in the organ wall or the blood vessel wall. In other words, the behavioral information is information based on the video in which the organ wall or the blood vessel wall is captured obtained using four-dimensional angiography.

For example, the behavioral information is numerical information in which a plurality of pairs of (i) a specific time in the video and (i) the three-dimensional coordinate position of each of a plurality of predetermined points in the organ wall or the blood vessel wall at that specific time are arranged according to the passage of time in which the heart pulsates one time in the video. Video information processing device 300 outputs the behavioral information to wall thickness estimation device 100. Video information processing device 300 is, for example, a personal computer, but may also be a server with high computing performances that is connected to a network.

Wall thickness estimation device 100 obtains the behavioral information generated by video information processing device 300, generates, for each position, estimation information for estimating the thickness of the organ wall or the blood vessel wall based on the obtained behavioral information, and outputs the generated estimation information to display 200. Wall thickness estimation device 100 is, for example, a personal computer, but may also be a server with high computing performances that is connected to a network.

Display 200 displays the estimation information output from wall thickness estimation device 100. Specifically, display 200 is a monitor including, for example, a liquid crystal panel or an organic electroluminescent (EL) panel. A television, a smartphone, or a tablet terminal may be used as display 200.

Wall thickness estimation device 100, display 200, and video information processing device 300 may be connected by wire or wirelessly, as long as they can send and receive the behavioral information or the estimation information.

Video information processing device 300 obtains a video in which an organ wall or a blood vessel wall is captured, and generates behavioral information which is numerical information about changes over time in the position of each of a plurality of predetermined points in the organ wall or the blood vessel wall. Wall thickness estimation device 100 obtains the behavioral information generated by video information processing device 300, and generates, for each position, estimation information for estimating the thickness of the organ wall or the blood vessel wall based on the obtained behavioral information. Wall thickness estimation device 100 further outputs the generated estimation information to display 200.

As a result, in wall thickness estimation system 1000, a video in which the organ wall or the blood vessel wall is captured is obtained using the minimally invasive method. Furthermore, wall thickness estimation system 1000 can generate, for each position, estimation information for estimating the thickness of the organ wall or the blood vessel wall using the behavioral information related to the video. Therefore, wall thickness estimation system 1000 can generate highly accurate information about the wall thickness in the vicinity of each of a plurality of predetermined points in the organ wall or the blood vessel wall.

Figure 2:
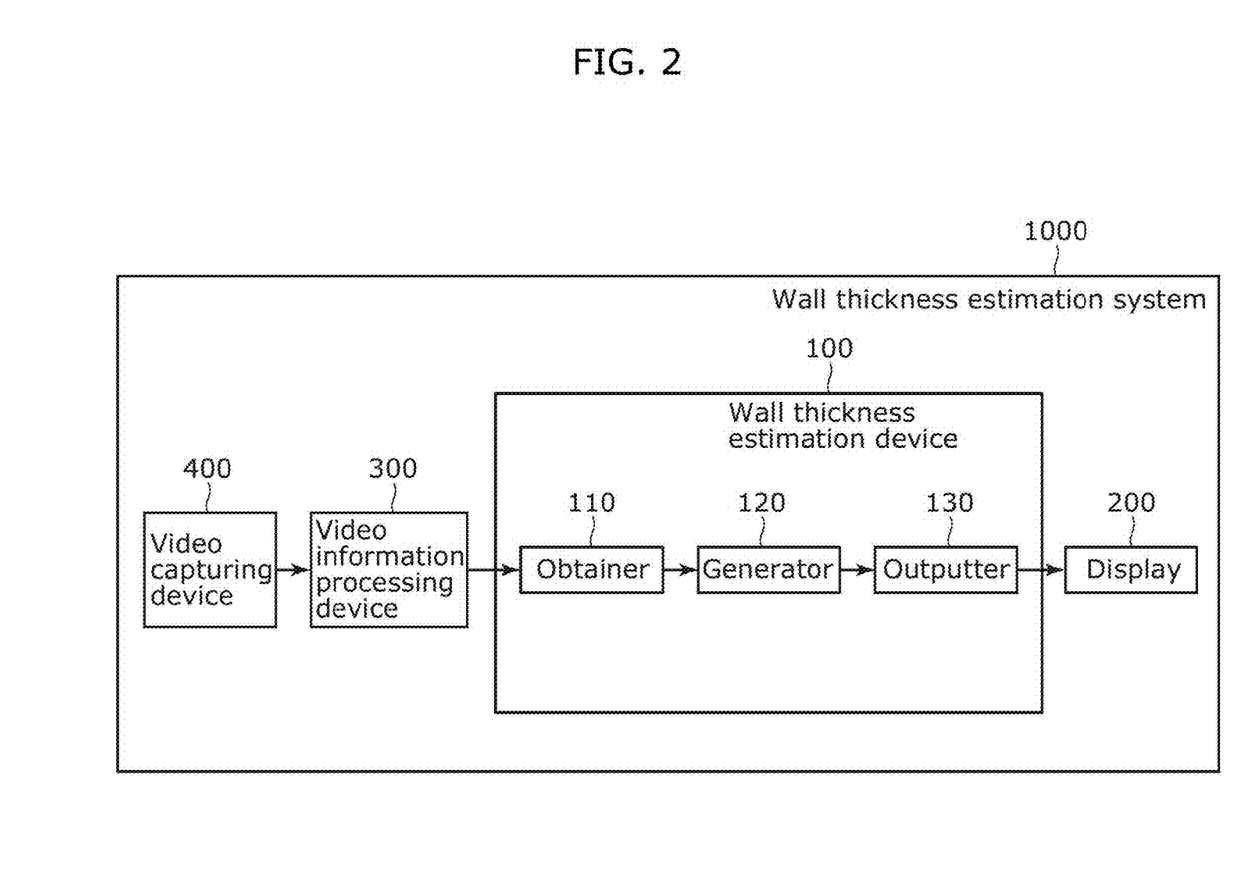
FIG. 2 is a block diagram illustrating the characteristic functional configuration of a wall thickness estimation device according to the embodiment.

Next, the functional configuration of wall thickness estimation device 100 according to the embodiment is described in detail.

FIG. 2 is a block diagram illustrating the characteristic functional configuration of wall thickness estimation device 100 according to the embodiment. Wall thickness estimation device 100 includes obtainer 110, generator 120, and outputter 130.

Obtainer 110 obtains behavioral information which is numerical information about changes over time in position of each of a plurality of predetermined points in an organ wall or a blood vessel wall, based on a video in which the organ wall or the blood vessel wall is captured obtained using four-dimensional angiography. Specifically, obtainer 110 obtains behavioral information generated by video information processing device 300. Obtainer 110 is, for example, a communication interface for performing wired or wireless communication.

Generator 120 generates, for each position, estimation information for estimating the thickness of the organ wall or the blood vessel wall based on the behavioral information obtained by obtainer 110. The estimation information is information that visualizes the mass of each of the plurality of predetermined points in the organ wall or the blood vessel wall.

The estimation information is, for example, image data of a graph of information about the mass of each of the plurality of predetermined points. It is to be noted that a method of generating the estimation information is described later with reference to FIGS. 6 to 8. Generator 120 is specifically implemented as, a processor, a microcomputer, or a dedicated circuit that executes a program.

Here, a description is given of an Inventor's hypothesis regarding the estimation information generated by generator 120. As described above, the estimation information is information that visualizes the mass of each of the plurality of predetermined points for estimating the thickness of the organ wall or the blood vessel wall. The Inventor has performed tests based on the hypothesis that the mass and the thickness of the organ wall or the blood vessel wall at each of the plurality of predetermined points in the organ wall or the blood vessel wall have a correlation with each other.

In other words, based on the hypothesis, the thickness of the organ wall or the blood vessel wall is larger as the mass is larger, and the thickness of the organ wall or the blood vessel wall is smaller as the mass is smaller. If the hypothesis is true, it is possible to estimate the thickness of the organ wall or the blood vessel wall by obtaining the estimation information according to this embodiment.

Outputter 130 outputs the estimation information generated by generator 120. Outputter 130 may output the estimation information generated by generator 120 to display 200. Outputter 130 is, for example, a communication interface for performing wired or wireless communication.

Next, the plurality of predetermined points which are one example of information about the behavioral information is described with reference to FIGS. 3 to 5. The blood vessel wall is described in this embodiment, but the same description applies to the organ wall. Here, the blood vessel wall is aneurysm wall 11 of cerebral aneurysm 10.

Figure 3:
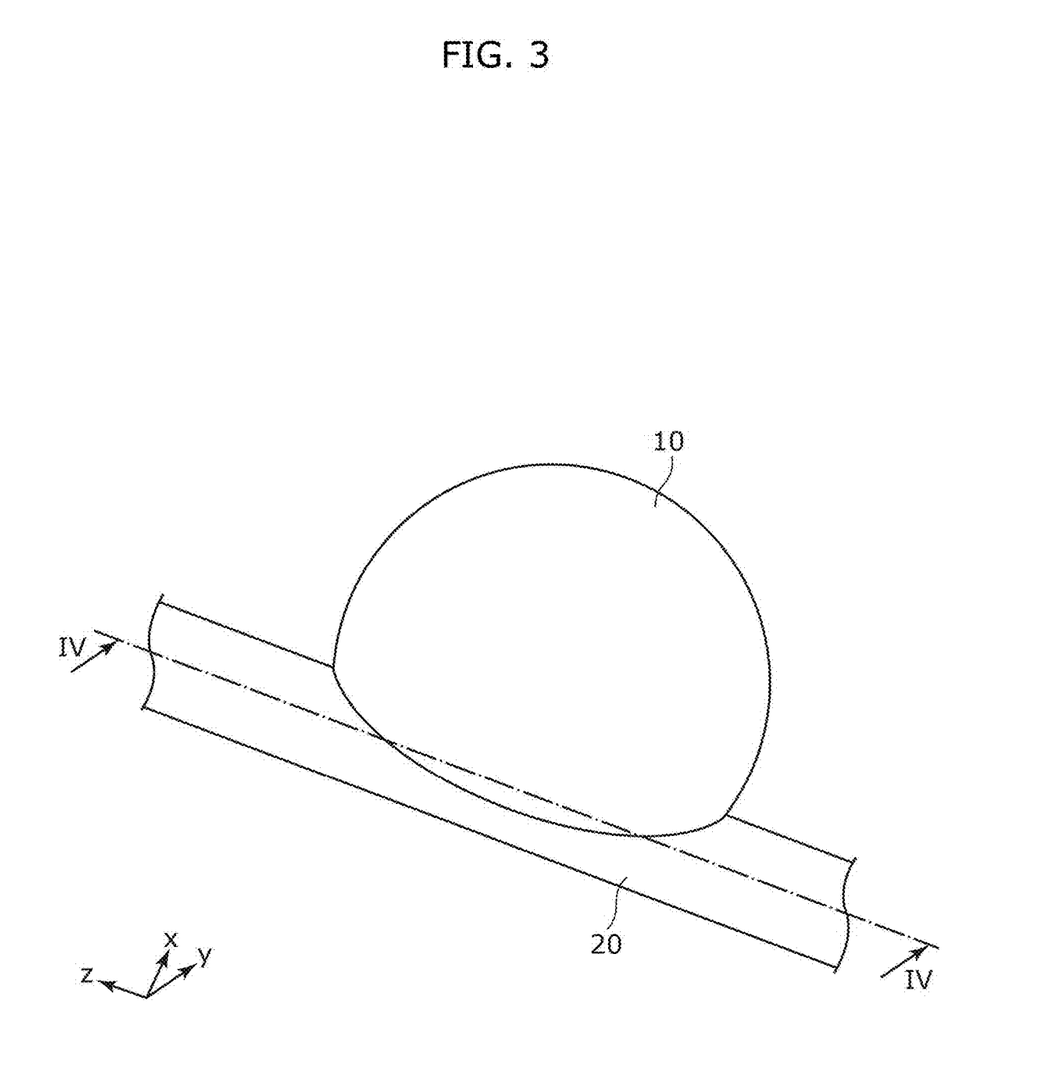
FIG. 3 is a perspective view of a cerebral aneurysm according to the embodiment.
Figure 4:
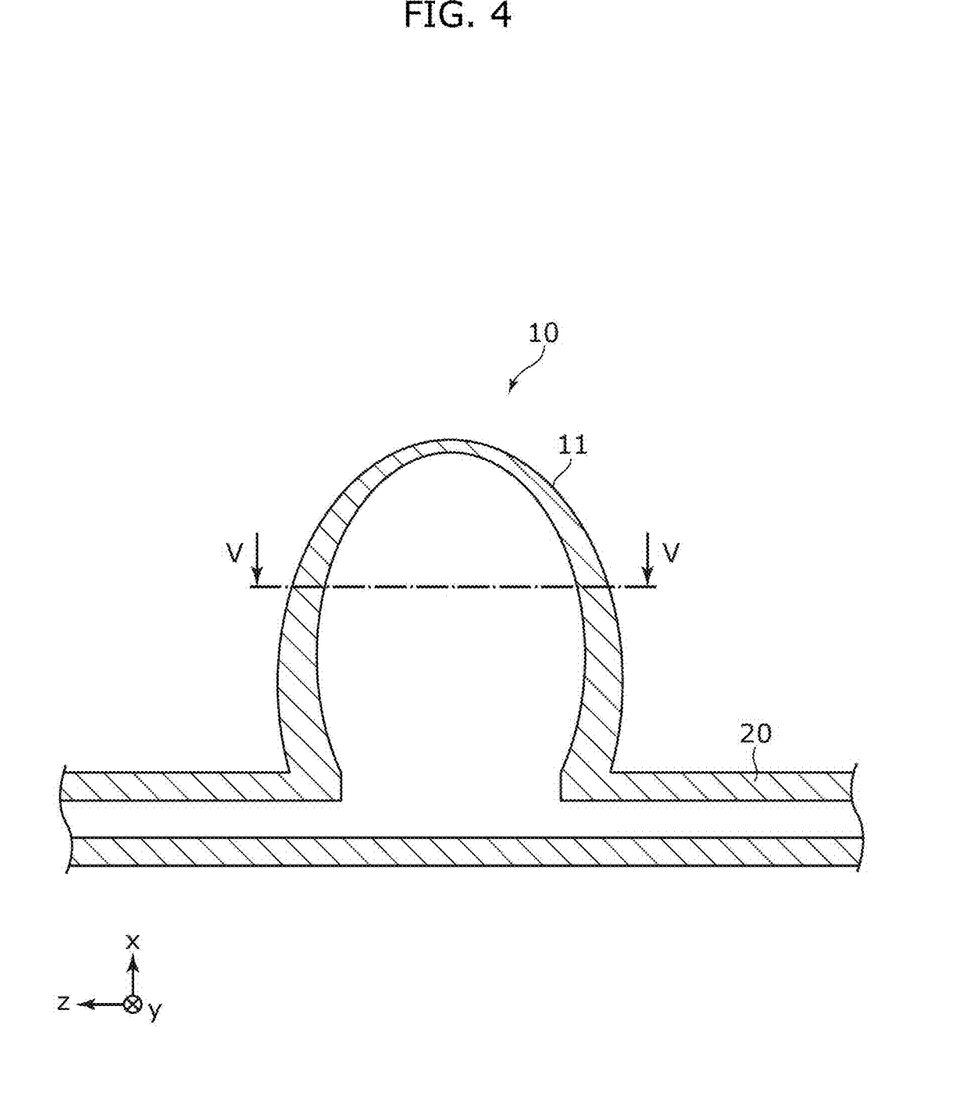
FIG. 4 is a cross sectional view of the cerebral aneurysm according to the embodiment taken at line IV-IV in FIG. 3.
Figure 5:
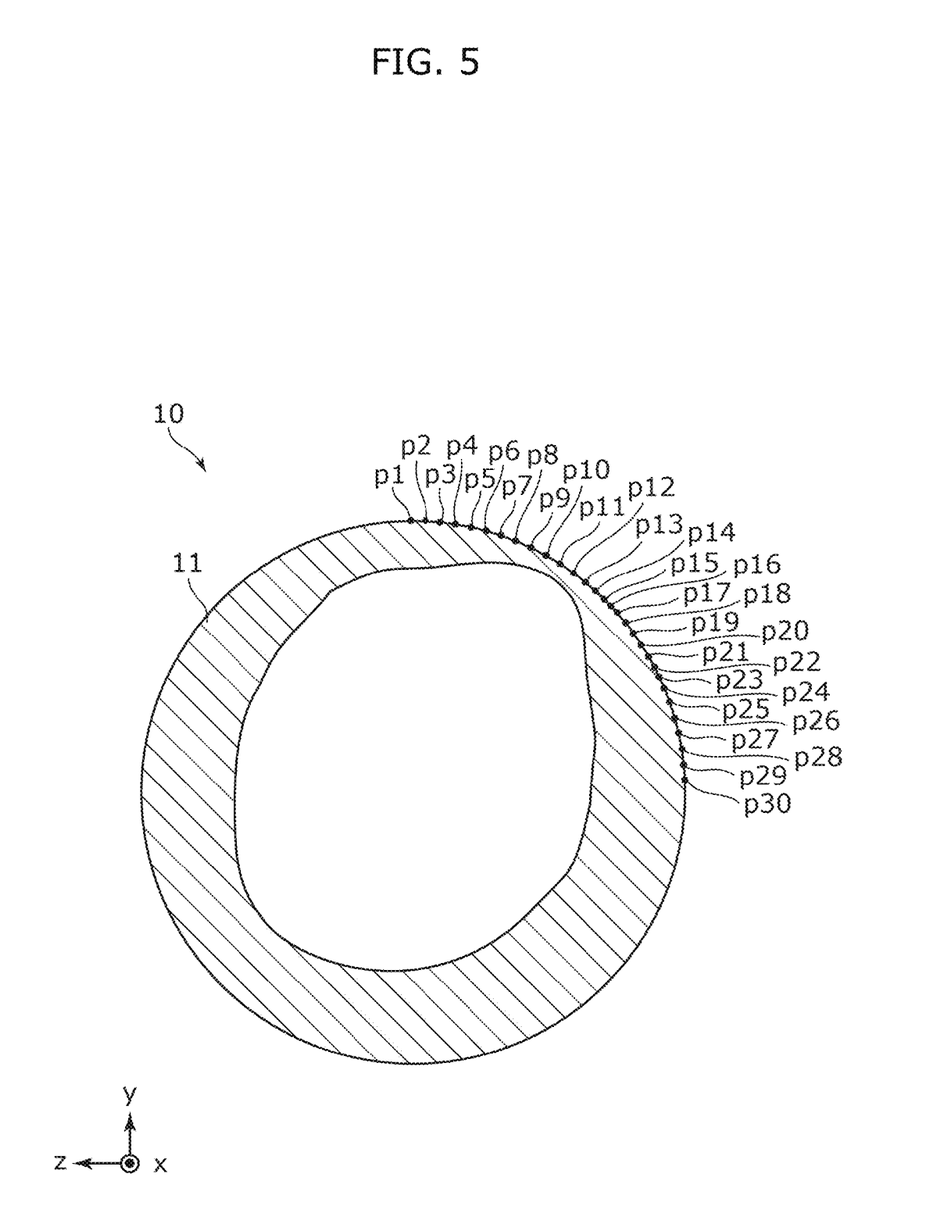
FIG. 5 is a cross sectional view of the cerebral aneurysm according to the embodiment taken at line V-V in FIG. 4.

In FIGS. 3 to 5, the x-axis positive direction is the direction in which cerebral aneurysm 10 extends from parent blood vessel 20, the z-axis is the direction in which parent blood vessel 20 extends, and the y-axis is the direction extending orthogonally to the x- and z-axes.

FIG. 3 is a perspective view of cerebral aneurysm 10 according to this embodiment. FIG. 4 is a cross sectional view of cerebral aneurysm 10 according to this embodiment taken at line IV-IV in FIG. 3. Parent blood vessel 20 is one blood vessel among the arteries in the brain of subject U. Cerebral aneurysm 10 is an aneurysm in which a portion of parent blood vessel 20 has bulged, extending in the x-axis direction from parent blood vessel 20.

FIG. 5 is a cross sectional view of cerebral aneurysm 10 according to this embodiment taken at line V-V in FIG. 4.

As FIG. 5 illustrates, in the cross section of cerebral aneurysm 10, points are provided so as to correspond to 0 o'clock to 3 o'clock on a clock face. Here, point p1 is provided in the 0 o'clock direction, point p30 is provided in the 3 o'clock direction, and 28 points which are p2 to p29 are provided between 0 o'clock and 3 o'clock at equal intervals. It is to be noted that the number of points is not limited thereto. For example, in one cross section, 10 to 1000 points may be provided. Furthermore, although one cross section is used in this embodiment, the number of cross sections is not limited thereto. A plurality of cross sections (for example, 10 to 1000 cross sections) may be used.

The plurality of predetermined points in the blood vessel wall (aneurysm wall 11) in this embodiment are point p1 to point 30. In other words, the total number of the plurality of predetermined points present in aneurysm wall 11 is 30.

At each of these 30 predetermined points, obtainer 110 obtains behavioral information, which is numerical information about changes in position over time. Based on this behavioral information, generator 120 generates, for each position, estimation information for estimating the thickness of aneurysm wall 11 in the vicinity of a predetermined point. The plurality of predetermined points in the blood vessel wall are not limited to the above points described above, and can be selected from two or more points in the blood vessel wall.

In the present embodiment, the behavioral information is numerical information about changes in position over time during a certain period of time. A certain period of time is, for example, the duration of one pulsation of the heart. Furthermore, the duration of one pulsation of the heart is divided evenly into 100 steps.

It is to be noted that the duration of one pulsation of the heart is not limited thereto. The duration may be divided evenly into a certain number of steps that is selected from 10 to 1000 steps. Here, the point in time when the pulsation starts is 0 step, and the point in time when the pulsation ends is 100 steps. Accordingly, the behavioral information includes information about the x-, y-, and z-axis positions of the 30 predetermined points at the respective 0 to 100 steps.

The certain period of time may be a specific number of seconds, for example, 1 second, 5 seconds, or 10 seconds. The certain period of time may be subdivided in any manner as long as it is three or more divisions. For example, unlike the above example, the certain period of time may be divided by a number of steps other than 100. Furthermore, the certain period of time does not always need to be divided evenly.

[Steps of Processing in Wall Thickness Estimation Method]

Figure 6:
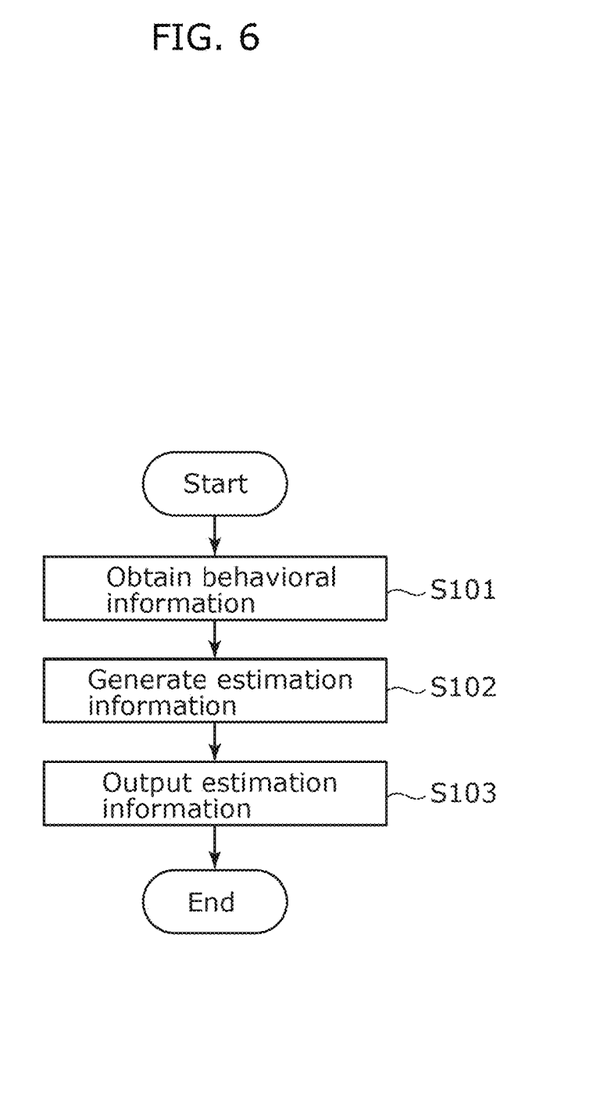
FIG. 6 is a flowchart illustrating steps of processing in which a wall thickness estimation device according to the embodiment estimates the thickness of a wall of a cerebral aneurysm, FIG. 7 indicates one example of estimation information according to the embodiment and a still image of a parent blood vessel with a cerebral aneurysm in a case.

Next, specific steps of processing in the wall thickness estimation method performed by wall thickness estimation device 100 is described. Although a description is given of a case of a blood vessel wall, the same description applies also to a case of an organ wall. FIG. 6 is a flowchart illustrating steps of processing in which wall thickness estimation device 100 according to the embodiment estimates the thickness of aneurysm wall 11 of cerebral aneurysm 10.

Obtainer 110 obtains behavioral information via video information processing device 300. The behavioral information is numerical information about changes over time in the position of each of a plurality of predetermined points in aneurysm wall 11 of cerebral aneurysm 10 of subject U (obtaining step S101).

Next, generator 120 generates estimation information which is information that visualizes the mass of each of the plurality of predetermined points for estimating the thickness of the blood vessel wall from the behavioral information obtained by obtainer 110 in obtaining step S101 (generating step S102). The processing performed by generator 120 is described more specifically below. Generator 120 generates estimation information according to Expression (1). It is to be noted that the position, the mass, the resistance, the spring constant, the external force, and the rational number of each of the predetermined points are x, ρ, μ, k, P, and m, respectively.

[Math. 1]

$$F(\partial_t^2 x, \partial_t x, |x|^m, x, P; \rho, \mu, k) = 0 \qquad \text{Expression (1)}$$

Here, the position x, the rational number m, and the external force P are variables, and the mass ρ, the resistance μ, and the spring constant k are constants. Furthermore, estimation information may be generated using any one of all the mathematical expressions that can be used as a replacement for Expression (1).

Generator 120 calculates the mass ρ, the resistance μ, and the spring constant k of each of the plurality of predetermined points that satisfy Expression (1). It is to be noted that, at this time, at least one of the mass ρ, the resistance μ, and the spring constant k may be calculated.

The mass p is the mass of a predetermined point, and is more specifically, may be the mass of a region including the predetermined point. The region including the predetermined point is, for example, in a range of 5 mm having the predetermined point as its center. It is to be noted that mass ρ is not limited the mass ρ.

The resistance μ and the spring constant k are a resistance and a spring constant that are generated by means of cerebral aneurysm 10 vibrating due to pulsation of the heart. However, resistances u and spring constants k are not limited to the resistance u and the spring constant k. The resistance μ may be a value stemming from friction occurred because cerebral aneurysm 10 is in contact with the brain. A value of a potential based on an electrocardiographic complex of subject U is used as the external force P. However, external forces P are not limited to the external force P. It is to be noted that, in this embodiment, generator 120 obtains the potential based on the electrocardiographic complex from video capturing device 400 via video information processing device 300 and obtainer 110.

Generator 120 further calculates mass ρ, a resistance μ, and a spring constant k, using parameter estimation. As one example, a mathematical analysis method may be used as the parameter estimation.

Generator 120 generates estimation information according to the mass ρ calculated as described above. Here, one example of the estimation information is image data of a graph of information regarding the mass ρ calculated.

As described above, it is possible to generate more highly accurate information regarding the blood vessel wall according to Expression (1) or the parameter estimation.

Next, outputter 130 outputs the estimation information generated by generator 120 (outputting step S103). In outputting step S103, outputter 130 transmits, for example, the image data generated by generator 120 in generating step S102 to display 200.

Display 200 obtains the image data output by outputter 130 and displays an image based on the image data.

Wall thickness estimation device 100 may execute the wall thickness estimation method by reading a computer program recorded on a computer-readable recording medium such as a CD-ROM.

Next, the relationship between the estimation information (more specifically, the calculated mass ρ) and the thickness of the blood vessel is described using a case of a symptom (hereinafter referred to as a case) regarding a cerebral aneurysm, Here, in the case, the mass ρ of each of the plurality of predetermined points corresponding to p1 to p30 in FIG. 5 is calculated.

Figure 7:
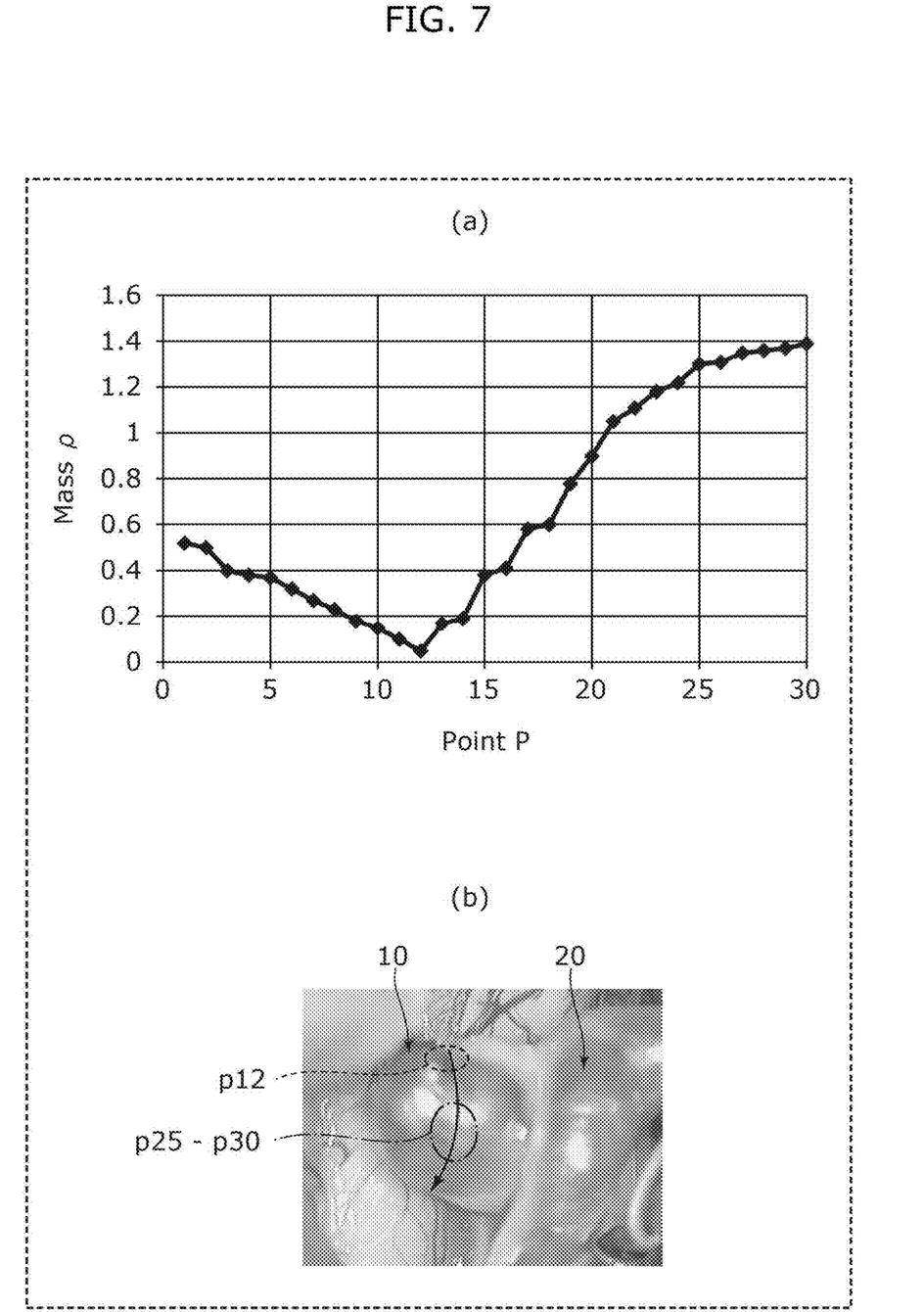

FIG. 7 indicates one example of estimation information according to the embodiment and a still image of parent blood vessel 20 with cerebral aneurysm 10 in a case. More specifically, (a) of FIG. 7 is a diagram that is one example of estimation information and illustrates the mass ρ of each of the plurality of points; and (b) of FIG. 7 is a diagram of a still image of cerebral aneurysm 10 in the case when craniotomy has been performed.

In (a) of FIG. 7, the values along the horizontal axis correspond to numerals at the ends of points p1 to p30 illustrated in FIG. 5, and each of the values along the vertical axis corresponds to the mass ρ of a corresponding one of points p1 to p30. It is to be noted that the mass ρ is relative mass. In this embodiment, the mass ρ decreases in order from point p1 to point p12. The mass ρ of point p12 is the smallest, the mass ρ increases in order from point p12 to point p30. For example, the mass ρ is larger in each of points p25 to p30.

The arrow in (b) of FIG. 7 indicates the direction in which the numerals at the ends of points p1 to p30 illustrated in FIG. 5 increase. In (b) of FIG. 7, the thicknesses of the blood vessel wall in cerebral aneurysm 10 are smaller as the colors of cerebral aneurysm 10 are deeper, and are larger as the colors of cerebral aneurysm 10 are lighter.

Although cerebral aneurysm 10 is represented in two colors that are white and black, it is to be noted that a still image of cerebral aneurysm 10 may be represented in full color in an actual craniotomy. For this reason, in (b) of FIG. 7, the cerebral aneurysm 10 part represented in deep color is a part having a weak white tone and a strong red tone in the actual craniotomy. In addition, in (b) of FIG. 7, the cerebral aneurysm 10 part represented in light color is a part having a strong white tone and a weak red tone in the actual craniotomy.

In (b) of FIG. 7, point p12 whose mass ρ is smallest corresponds to a region enclosed by a broken line, and points p25 to p30 whose mass ρ are larger correspond to a region enclosed by a dashed line. As illustrated in (b) of FIG. 7, the region enclosed by the broken line is a region in which the color of cerebral aneurysm 10 is deep and thus the thickness of the blood vessel is small, and the region enclosed by the dashed line is a region in which the color of cerebral aneurysm 10 is light and thus the thickness of the blood vessel is large. In other words, point p12 whose mass ρ is smallest corresponds to the region in which the thickness of the blood vessel is small, and points p25 top 30 whose mass ρ are larger correspond to the region in which the thicknesses of the blood vessel are large. In other words, the Invertors' hypothesis that the thickness of the blood vessel is larger as the mass ρ is larger and the thickness of the blood vessel is smaller as the mass ρ is smaller is clearly correct.

Thus, the use of the estimation information (more specifically, the calculated mass ρ) makes it possible to generate highly accurate information about the thickness of the blood vessel wall.

Such information is useful information for, for example, discriminating a cerebral aneurysm which is likely to grow and rapture and a cerebral aneurysm which is unlikely to grow and rapture, and appropriately determining the necessity of treatment.

In other words, the wall thickness estimation method according to this embodiment makes it possible to propose useful information for providing a specific treatment for a disease of a blood vessel by generating highly accurate information about a wall of the blood vessel according to a minimally invasive method.

Furthermore, the wall thickness estimation method according to this embodiment can be used to estimate the thickness of an organ wall without being limited to the thickness of the blood vessel wall.

In other words, the wall thickness estimation method according to this embodiment makes it possible to propose useful information for providing a specific treatment for a disease of an organ by generating highly accurate information about a wall of the organ according to a minimally invasive method in which no abdominal operation, open heart surgery, craniotomy, etc., are used.

Figure 8:
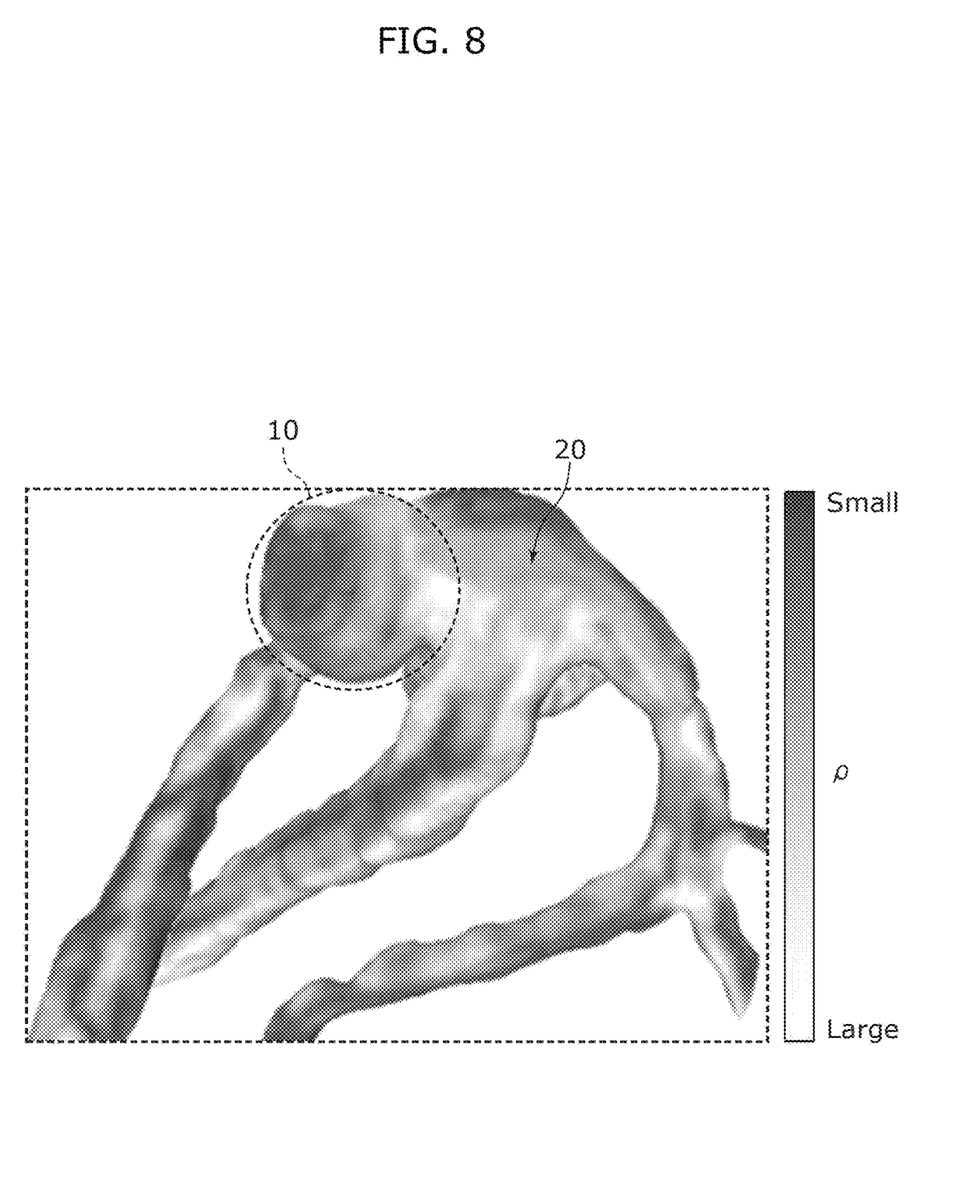
FIG. 8 is a schematic diagram of another example of estimation information according to the embodiment. The estimation information indicates the mass of each of predetermined points in a parent blood vessel with a cerebral aneurysm

In addition, estimation information is not limited to the estimation information described above. For example, generator 120 may generate other exemplary estimation information using the calculated mass ρ (for example, (a) in FIG. 7). FIG. 8 is a schematic diagram of another example of estimation information according to the embodiment. The estimation information indicates mass ρ of each of predetermined points in parent blood vessel 20 with cerebral aneurysm 10. It is to be noted that the schematic diagram illustrated in FIG. 8 may be generated using the minimum value, the maximum value, the standard deviation, the average, and the median of each of mass ρ, resistance μ, and spring constant k.

In FIG. 8, the mass ρ is smaller as the color of parent blood vessel 20 with cerebral aneurysm 10 is deeper, and is larger as the color of parent blood vessel 20 with cerebral aneurysm 10 is lighter. Although parent blood vessel 20 with cerebral aneurysm 10 are represented in white and black in FIG. 8, it is to be noted that a schematic diagram of parent blood vessel 20 with cerebral aneurysm 10 may be represented in full color when outputter 130 actually outputs the schematic diagram.

For this reason, the cerebral aneurysm 10 part and parent blood vessel 20 part whose colors are deep in FIG. 8 are parts having a week white tone and a strong red tone when outputter 130 actually outputs the schematic diagram. On the other hand, the cerebral aneurysm 10 part and parent blood vessel 20 part whose colors are light in FIG. 8 are parts having a strong white tone and a weak red tone when outputter 130 actually outputs the schematic diagram.

As described above, since the Inventor's hypothesis is true, the thicknesses of the blood vessel wall are smaller as the colors of cerebral aneurysm 10 and parent blood vessel 20 are deeper, and are larger as the colors of cerebral aneurysm 10 and parent blood vessel 20 are lighter.

The estimation information represented as such a schematic diagram is useful information for, for example, discriminating a cerebral aneurysm which is likely to grow and rapture and a cerebral aneurysm which is unlikely to grow and rapture, and appropriately determining the necessity of treatment.

Although two-dimensional schematic diagram is illustrated in FIG. 8, a three-dimensional color map may be used as estimation information.

Advantageous Effects, Etc.

As described above, the wall thickness estimation method includes obtaining step S101, generating step S102, and outputting step S103. Obtaining step S101 is a step of obtaining behavioral information based on a video in which an organ wall or a blood vessel wall is captured using four-dimensional angiography. The behavioral information is numerical information about changes over time in the position of each of a plurality of predetermined points in the organ wall or the blood vessel wall. Generating step S102 is a step of generating, based on the behavioral information obtained in the obtaining, estimation information that visualizes the mass of each of the plurality of predetermined points for estimating a thickness of the organ wall or a thickness of the blood vessel wall. Outputting step S103 is a step of outputting the estimation information generated in the generating.

A computer program according to this embodiment causes a computer to execute the above-described wall thickness estimation method.

In this way, in the wall thickness estimation method, for example, a video in which the blood vessel wall is captured is generated using the X-ray CT device or the MRI device, and four-dimensional angiography. For example, the video in which the blood vessel is captured is obtained using a minimally invasive method compared to other methods such as craniotomy. The wall thickness estimation method makes it possible to generate estimation information that visualizes the mass of each of the plurality of predetermined points for estimating the thickness of the blood vessel wall, using the behavioral information related to the video. It is shown that the thickness of the blood vessel wall estimated based on the estimation information corresponds to the thickness of the blood vessel wall obtained by craniotomy.

In other words, the wall thickness estimation method can generate highly accurate information about the wall thickness in the vicinity of each of the plurality of predetermined points in the blood vessel wall. In this embodiment, for example, the thickness of aneurysm wall 11 of cerebral aneurysm 10 is estimated. Such information is useful information for, for example, discriminating a cerebral aneurysm which is likely to grow and rapture and a cerebral aneurysm which is unlikely to grow and rapture, and appropriately determining the necessity of treatment.

It is to be noted that the wall thickness estimation method can be used to estimate the thickness of an organ wall without being limited to the thickness of the blood vessel wall.

In other words, the wall thickness estimation method according to this embodiment makes it possible to propose useful information for providing a specific treatment for a disease of an organ or a disease of a blood vessel by generating highly accurate information about a wall of the organ or a wall of the blood vessel according to a minimally invasive method.

In addition, the position, the mass, a resistance, a spring constant, an external force, and a rational number of each of the plurality of predetermined points are x, $\rho$, $\mu$, k, P, and m, respectively. At this time, generating step S102 includes calculating the mass $\rho$, the resistance $\mu$, and the spring constant k that satisfy Expression (1).

In this way, it is possible to generate more highly accurate information about the organ wall or the blood vessel wall.

In addition, generating step S102 further includes calculating the mass $\rho$, the resistance $\mu$, and the spring constant k, using parameter estimation.

In this way, it is possible to generate more highly accurate information about the organ wall or the blood vessel wall.

In addition, in the wall thickness estimation method, the thickness of the blood vessel wall is a thickness of a wall of an aneurysm or a thickness of a wall of a varicose vein.

In this way, the wall thickness estimation method can estimate the thickness of the wall of the aneurysm or the thickness of the wall of the varicose vein as the thickness of the blood vessel wall.

In addition, in the wall thickness estimation method, the thickness of the blood vessel wall is a thickness of a wall of a cerebral aneurysm.

In this way, the wall thickness estimation method can estimate the thickness of the wall of the cerebral aneurysm as the thickness of the blood vessel wall.

In addition, in the wall thickness estimation method, the thickness of the blood vessel wall is a thickness of the blood vessel wall of an artery or a thickness of the blood vessel wall of a vein.

In this way, the wall thickness estimation method can estimate the thickness of the blood vessel wall of the artery or the thickness of the blood vessel wall of the vein as the thickness of the blood vessel wall.

Wall thickness estimation device 100 includes obtainer 110, generator 120, and outputter 130. Obtainer 110 obtains behavioral information based on a video in which an organ wall or a blood vessel wall is captured using four-dimensional angiography. The behavioral information is numerical information about changes over time in a position of each of a plurality of predetermined points in the organ wall or the blood vessel wall. Generator 120 generating, based on the behavioral information obtained in the obtaining, estimation information that visualizes mass of each of the plurality of predetermined points for estimating a thickness of the organ wall or a thickness of the blood vessel wall. Outputter 130 outputs the estimation information generated by generator 120.

In this way, in wall thickness estimation device 100, for example, a video in which the blood vessel wall is captured is generated using (i) the X-ray CT device or the MRI device and (ii) four-dimensional angiography. For example, the video in which the blood vessel is captured is obtained using a minimally invasive method compared with methods such as craniotomy. Wall thickness estimation device 100 is capable of generating estimation information that visualizes the mass of each of the plurality of predetermined points for estimating the thickness of the blood vessel wall, using the behavioral information related to the video. It is shown that the thickness of the blood vessel wall estimated based on the estimation information corresponds to the thickness of the blood vessel wall obtained by craniotomy.

In other words, wall thickness estimation device 100 is capable of generating highly accurate information about the wall thickness in the vicinity of each of the plurality of predetermined points in the blood vessel wall. In this embodiment, for example, the thickness of aneurysm wall 11 of cerebral aneurysm 10 is estimated. Such information is useful information for, for example, discriminating a cerebral aneurysm which is likely to grow and rapture and a cerebral aneurysm which is unlikely to grow and rapture, and appropriately determining the necessity of treatment.

It is to be noted that wall thickness estimation device 100 can be used to estimate the thickness of an organ wall without being limited to the thickness of the blood vessel wall.

In other words, wall thickness estimation device 100 according to this embodiment is capable of proposing useful information for providing a specific treatment for a disease of an organ or a disease of a blood vessel by generating highly accurate information about a wall of the organ or a wall of the blood vessel according to a minimally invasive method.

Furthermore, wall thickness estimation system 1000 includes: wall thickness estimation device 100; video information processing device 300 which obtains the video, generates the behavioral information, and outputs the behavioral information to obtainer 110; and display 200 which displays the estimation information output by outputter 130.

In this way, in wall thickness estimation system 1000, for example, a video in which the blood vessel wall is captured is generated using the X-ray CT device or the MRI device, and four-dimensional angiography. For example, the video in which the blood vessel is captured is obtained using a minimally invasive method compared with methods such as craniotomy. Wall thickness estimation system 1000 is capable of generating estimation information that visualizes the mass of each of the plurality of predetermined points for estimating the thickness of the blood vessel wall, using the behavioral information related to the video. It is shown that the thickness of the blood vessel wall estimated based on the estimation information corresponds to the thickness of the blood vessel wall obtained by craniotomy.

In other words, wall thickness estimation system 1000 is capable of generating highly accurate information about the wall thickness in the vicinity of each of the plurality of predetermined points in the blood vessel wall. In this embodiment, for example, the thickness of aneurysm wall 11 of cerebral aneurysm 10 is estimated. Such information is useful information for, for example, discriminating a cerebral aneurysm which is likely to grow and rapture and a cerebral aneurysm which is unlikely to grow and rapture, and appropriately determining the necessity of treatment.

It is to be noted that wall thickness estimation system 1000 can be used to estimate the thickness of an organ wall without being limited to the thickness of the blood vessel wall.

In other words, wall thickness estimation system 1000 according to this embodiment is capable of proposing useful information for providing a specific treatment for a disease of an organ or a disease of a blood vessel by generating highly accurate information about a wall of the organ or a wall of the blood vessel according to a minimally invasive method.

Furthermore, by means of estimation information being visualized and displayed, for example, a doctor, etc., can obtain the highly accurate information about the thickness of the organ wall or the thickness of the blood vessel wall.

[Other Embodiments] Although the wall thickness estimation method and the like according to the embodiment have been described above, the present invention is not limited to the above embodiment.

The analysis based on the parameter estimation used in this embodiment is included in an artificial intelligence (AI). In other words, in generating step S102, the analysis for calculating mass $\rho$, a resistance $\mu$, and a spring constant k is not limited to the parameter estimation, and another method in which AI technology is used may be used.

The above embodiment describes methods of obtaining behavioral information using actual cases and four-dimensional angiography. However, the methods of obtaining the behavioral information are not limited to these examples. For example, the behavioral information may be obtained by the two other exemplary methods described below.

In a first other exemplary method, behavioral information is obtained by using an artificial aneurysm that has been artificially created, an artificial heart connected to the artificial aneurysm, and an imaging device.

An artificial aneurysm is an artificial aneurysm that has occurred in an artificial blood vessel. The artificial blood vessel and the artificial aneurysm are created to mimic a human blood vessel and a human aneurysms that has occurred in the human blood vessel. The artificial aneurysm may be made of, for example, a rubber material. For example, a silicone rubber, a fluorine rubber, or the like may be used.

The artificial aneurysm may also be made of, for example, a silicone resin. As long as the artificial aneurysm is made of a flexible material, the material used for the artificial aneurysm is not limited to the above examples.

The artificial aneurysm is created utilizing image data obtained by an X-ray CT device or an MRI device as described above. This image data includes data on the human blood vessel and the aneurysm that has occurred in the blood vessel.

The artificial aneurysm is created based on digital imaging and communications in medicine (DICOM) data related to the image data obtained above.

An artificial heart is a device that performs the pumping function of the human heart. The artificial heart and the artificial aneurysm are connected, and the artificial heart's pumping function is activated to cause the artificial aneurysm to move in a pulsating manner. The behavioral information is obtained using this movement of the artificial aneurysm and the imaging device.

The imaging device is, for example, a camera capable of capturing still images and videos. Alternatively, the imaging device may be a device capable of obtaining all the following pieces of information: three-dimensional coordinates on a surface of an observation target, a displacement in the three-dimensional space, and a speed in the three-dimensional space, an acceleration in the three-dimensional space. Such an imaging device is capable of obtaining all the pieces of information which are three-dimensional coordinates on a surface of an observation target, a displacement in the three-dimensional space, a speed in the three-dimensional space, and an acceleration in the three-dimensional space, by capturing a video for 1 second, 5 seconds, or 10 seconds.

As described above, in the first other exemplary method, all the pieces of information which are the three-dimensional coordinates on the surface of the observation target, the displacement in the three-dimensional space, the speed in the three-dimensional space, and the acceleration in the three-dimensional space, by means of the imaging device capturing the video of the artificially created aneurysm that pulsates. Behavioral information may be obtained based on any or all of the pieces of information among the three-dimensional coordinates on the surface of the observation target, the displacement in the three-dimensional space, the speed in the three-dimensional space, and the acceleration in the three-dimensional space.

In the first other exemplary method according to the first other example, such behavioral information can be obtained more easily than in the craniotomy method described above because the technique is less invasive.

In a second other exemplary method, a model animal having a blood vessel in which an aneurysm has occurred and the imaging device described above are used to obtain behavioral information.

More specifically, the imaging device images a blood vessel with an aneurysm in the model animal to obtain the following all pieces of information: three-dimensional coordinates in a three-dimensional space on the surface of the blood vessel with aneurysm in the model animal, a displacement in the three-dimensional space, a speed in the three-dimensional space, and an acceleration in the three-dimensional space. The behavioral information may be obtained based on any or all of the above pieces of information.

In the second other exemplary method, unlike a case involving a human as shown in the embodiment, a consent form and the like for the human subject of the case is not required. Additionally, since the surface of the blood vessel and aneurysm of the model animal can be patterned (for example, marked by spraying) for imaging, time evolution data of precise three-dimensional coordinates can be obtained.

Furthermore, data on the blood vessel and aneurysm of the model animal can be obtained at equal time intervals (for example, once every two weeks). This makes it easier to obtain behavioral information than in the embodiment.

The above method can be used to easily obtain a large number of behavioral information, and consequently, a large number of estimation information can be obtained. This is expected to improve the accuracy of the information about the wall.

Although the embodiment describes the thickness of the blood vessel wall as the thickness of aneurysm wall 11 of cerebral aneurysm 10, the thickness of the blood vessel wall may be the thickness of the wall of the blood vessel that is an artery or a vein, as described above. For example, when the thickness of the wall is the thickness of the wall of the blood vessel that is an artery or a vein, the degree of stenosis of the artery or the vein is estimated using the blood vessel wall thickness estimation method and the like according to the embodiment.

In each of the above embodiments, each element may be configured in the form of dedicated hardware or implemented by executing a software program suitable for the element. Each element may be implemented by means of a program executing unit, such as a central processing unit (CPU) or a processor, reading and executing a software program recorded on a recording medium such as a hard disk or semiconductor memory.

It is to be noted that embodiments resulting from variations of the above embodiments arrived at by those skilled in the art, as well as embodiments resulting from optional combinations of elements and functions in the above embodiments are included within the present invention as long as the embodiments do not depart from the scope of the present invention.

INDUSTRIAL APPLICABILITY

The wall thickness estimation method according to the present invention can be used in various applications, such as medical devices and medical methods.

The invention claimed is:

1. A wall thickness estimation method comprising:
obtaining behavioral information based on a video in which an organ wall or a blood vessel wall is captured using four-dimensional angiography, the behavioral information being numerical information about changes over time in a position of each of a plurality of predetermined points in the organ wall or the blood vessel wall;
generating, based on the behavioral information obtained in the obtaining, estimation information that visualizes mass of each of the plurality of predetermined points for estimating a thickness of the organ wall or a thickness of the blood vessel wall; and
outputting the estimation information generated in the generating,
wherein when the position, the mass, a resistance, a spring constant, an external force, and a rational number of each of the plurality of predetermined points are x, ρ, μ, k, P, and m, respectively,
the generating includes calculating the mass p which satisfies Expression (1):

[Math. 1]

$$F(\partial_t^2 x, \partial_t x, |x|^m, x, P; \rho, \mu, k) = 0. \qquad \text{Expression (1)}$$

2. The wall thickness estimation method according to claim 1,
the generating includes calculating the resistance μ, and the spring constant k which satisfy Expression (1).

3. The wall thickness estimation method according to claim 2,
wherein the generating includes calculating the mass ρ, the resistance μ, and the spring constant k, using parameter estimation.

4. The wall thickness estimation method according to claim 1,
wherein the thickness of the blood vessel wall is a thickness of a wall of an aneurysm or a thickness of a wall of a varicose vein.

5. The wall thickness estimation method according to claim 1,
wherein the thickness of the blood vessel wall is a thickness of a wall of a cerebral aneurysm.

6. The wall thickness estimation method according to claim 1,
wherein the thickness of the blood vessel wall is a thickness of a blood vessel wall of an artery or a thickness of a blood vessel wall of a vein.

7. A non-transitory recording medium having a computer program recorded thereon for causing a computer to execute the wall thickness estimation method according to claim 1.

8. A wall thickness estimation device comprising:
an obtainer which obtains behavioral information based on a video in which an organ wall or a blood vessel wall is captured using four-dimensional angiography, the behavioral information being numerical information about changes over time in a position of each of a plurality of predetermined points in the organ wall or the blood vessel wall;
a generator which generates, based on the behavioral information obtained by the obtainer, estimation information that visualizes mass of each of the plurality of predetermined points for estimating a thickness of the organ wall or a thickness of the blood vessel wall; and
an outputter which outputs the estimation information generated in the generating,
wherein when the position, the mass, a resistance, a spring constant, an external force, and a rational number of each of the plurality of predetermined points are x, ρ, μ, k, P, and m, respectively, the generating includes calculating the mass p which satisfies Expression (1):

[Math. 2]

$$F(\partial_t^2 x, \partial_t x, |x|^m, x, P; \rho, \mu, k) = 0. \qquad \text{Expression (1)}$$

9. A wall thickness estimation system comprising:

the wall thickness estimation device according to claim 8;

a video information processing device which obtains the video, generates the behavioral information, and outputs the behavioral information to the obtainer; and a display which displays the estimation information output by the outputter.

10. A wall thickness estimation method comprising:

obtaining behavioral information based on a video in which an organ wall or a blood vessel wall is captured using four-dimensional angiography, the behavioral information being numerical information about changes over time in a position of each of a plurality of predetermined points in the organ wall or the blood vessel wall;

generating, based on the behavioral information obtained in the obtaining, estimation information that visualizes mass of each of the plurality of predetermined points for estimating a thickness of the organ wall or a thickness of the blood vessel wall; and outputting the estimation information generated in the generating, wherein when an external force of each of the plurality of predetermined points is P, the generating includes generating the estimation information based on the external force P.

11. A wall thickness estimation method comprising:

obtaining behavioral information based on a video in which an organ wall or a blood vessel wall is captured using four-dimensional angiography, the behavioral information being numerical information about changes over time in a position of each of a plurality of predetermined points in the organ wall or the blood vessel wall;

generating, based on the behavioral information obtained in the obtaining, estimation information that visualizes mass of each of the plurality of predetermined points for estimating a thickness of the organ wall or a thickness of the blood vessel wall; and outputting the estimation information generated in the generating, wherein when a resistance of each of the plurality of predetermined points is u, the generating includes generating the estimation information based on the resistance u.

* * * * *